United States Patent
Badie et al.

(10) Patent No.: US 11,766,207 B2
(45) Date of Patent: Sep. 26, 2023

(54) METHODS, DEVICES AND SYSTEMS FOR IMPROVING R-WAVE DETECTION AND ARRHTYMIA DETECTION ACCURACY

(71) Applicant: Pacesetter, Inc., Sylmar, CA (US)

(72) Inventors: Nima Badie, Berkeley, CA (US); Fujian Qu, San Jose, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 414 days.

(21) Appl. No.: 17/223,885

(22) Filed: Apr. 6, 2021

(65) Prior Publication Data

US 2021/0369175 A1 Dec. 2, 2021

Related U.S. Application Data

(60) Provisional application No. 63/034,866, filed on Jun. 4, 2020, provisional application No. 63/033,184, filed on Jun. 1, 2020.

(51) Int. Cl.
*A61B 5/287* (2021.01)
*A61B 5/352* (2021.01)
(Continued)

(52) U.S. Cl.
CPC .............. *A61B 5/352* (2021.01); *A61B 5/076* (2013.01); *A61B 5/287* (2021.01); *A61B 5/686* (2013.01);
(Continued)

(58) Field of Classification Search
None
See application file for complete search history.

(56) References Cited

U.S. PATENT DOCUMENTS

| 5,755,739 A | 5/1998 | Sun et al. |
| 6,671,548 B1 | 12/2003 | Mouchawar et al. |

(Continued)

FOREIGN PATENT DOCUMENTS

| EP | 1615693 B1 | 1/2011 |
| EP | 2079520 B1 | 11/2013 |

(Continued)

OTHER PUBLICATIONS

Notice of Allowance dated Dec. 21, 2022, U.S. Appl. No. 17/153,036, filed Jan. 20, 2021.

(Continued)

*Primary Examiner* — Ankit D Tejani
(74) *Attorney, Agent, or Firm* — Vierra Magen Marcus LLP

(57) ABSTRACT

Described herein are methods, devices, and systems for improving R-wave detection sensitivity and positive predictive value, and for improving arrhythmia detection accuracy. Certain embodiments involve determining whether to classify a potential R-wave as a false R-wave (or more specifically, an over-sensed P-wave) by determining a measure of magnitude of a first portion of the signal corresponding to a first window following the potential R-wave, determining the measure of magnitude of a second portion of the signal corresponding to a second window following the first window, and classifying the potential R-wave as a false R-wave if the measure of magnitude of the second portion of the signal is at least a specified extent larger (e.g., at least 3 times larger) than the measure of magnitude of the first portion of the signal. Certain embodiments also involve adjusting an R-wave marker for a potential R-wave that is classified as a false R-wave.

22 Claims, 3 Drawing Sheets

(51) Int. Cl.
*G16H 50/30* (2018.01)
*A61B 5/07* (2006.01)
*A61B 5/00* (2006.01)
*G16H 40/67* (2018.01)
*A61B 5/361* (2021.01)

(52) U.S. Cl.
CPC ............ *A61B 5/7203* (2013.01); *G16H 50/30* (2018.01); *A61B 5/361* (2021.01); *G16H 40/67* (2018.01)

(56) References Cited

U.S. PATENT DOCUMENTS

| | | | |
|---|---|---|---|
| 7,027,858 B2 | 4/2006 | Cao et al. | |
| 7,155,282 B1 | 12/2006 | Min et al. | |
| 7,167,747 B2 | 1/2007 | Gunderson et al. | |
| 7,218,966 B2 | 5/2007 | Haefner | |
| 7,266,409 B2 | 9/2007 | Gunderson | |
| 7,283,863 B2 | 10/2007 | Gunderson et al. | |
| 7,333,855 B2 | 2/2008 | Gunderson et al. | |
| 7,412,282 B2 | 8/2008 | Houben | |
| 7,537,569 B2 | 5/2009 | Sarkar et al. | |
| 7,567,835 B2 | 7/2009 | Gunderson et al. | |
| 7,582,061 B2 | 9/2009 | Li et al. | |
| 7,623,911 B2 | 11/2009 | Sarkar et al. | |
| 7,630,756 B2 | 12/2009 | Linker | |
| 7,634,310 B2 | 12/2009 | Lee et al. | |
| 7,774,049 B2 | 8/2010 | Ghanem et al. | |
| 7,774,062 B2 | 8/2010 | Kim et al. | |
| 7,783,354 B2 | 8/2010 | Gunderson | |
| 7,818,056 B2 | 10/2010 | Kim et al. | |
| 7,831,301 B2 | 11/2010 | Cao et al. | |
| 7,894,893 B2 | 2/2011 | Kim et al. | |
| 7,912,545 B2 | 3/2011 | Li et al. | |
| 8,078,277 B2 | 12/2011 | Gunderson et al. | |
| 8,160,686 B2 | 4/2012 | Allavatam et al. | |
| 8,260,404 B1 | 9/2012 | Bharmi et al. | |
| 8,265,737 B2 | 9/2012 | Warren et al. | |
| 8,406,872 B2 | 3/2013 | Stadler et al. | |
| 8,437,840 B2 | 5/2013 | Patel et al. | |
| 8,437,851 B2 | 5/2013 | Corbucci et al. | |
| 8,473,042 B2 | 6/2013 | McCarthy et al. | |
| 8,506,500 B2 | 8/2013 | Li et al. | |
| 8,521,281 B2 | 8/2013 | Patel et al. | |
| 8,538,524 B2 | 9/2013 | Rosenberg et al. | |
| 8,560,058 B2 | 10/2013 | Babaeizadeh et al. | |
| 8,560,069 B2 | 10/2013 | Zhang | |
| 8,577,455 B2 | 11/2013 | Mitrani et al. | |
| 8,583,221 B1 | 11/2013 | Patel et al. | |
| 8,588,895 B2 | 11/2013 | Sanghera et al. | |
| 8,588,896 B2 | 11/2013 | Allavatam et al. | |
| 8,626,280 B2 | 1/2014 | Allavatam et al. | |
| 8,639,316 B2 | 1/2014 | Sarkar | |
| 8,744,559 B2 | 6/2014 | Houben et al. | |
| 8,750,994 B2 | 6/2014 | Ghosh et al. | |
| 8,774,909 B2 | 7/2014 | Patel et al. | |
| 8,781,585 B2 | 7/2014 | Gunderson et al. | |
| 8,792,971 B2 | 7/2014 | Gunderson et al. | |
| 8,886,296 B2 | 11/2014 | Patel | |
| 8,897,863 B2 | 11/2014 | Linker | |
| 8,914,106 B2 | 12/2014 | Charlton et al. | |
| 8,942,793 B2 | 1/2015 | Eberle et al. | |
| 9,101,278 B2 | 8/2015 | Fischell et al. | |
| 9,167,747 B1 | 10/2015 | Andros et al. | |
| 9,307,920 B2 | 4/2016 | Mahajan et al. | |
| 9,314,210 B2 | 4/2016 | Li | |
| 9,339,662 B2 | 5/2016 | Allavatam et al. | |
| 9,381,370 B2 | 7/2016 | Gunderson | |
| 9,468,766 B2 | 10/2016 | Sheldon et al. | |
| 9,597,525 B2 | 3/2017 | Cao et al. | |
| 9,675,261 B2 | 6/2017 | Cao et al. | |
| 9,682,238 B2 | 6/2017 | Zhang et al. | |
| 9,724,007 B2 | 8/2017 | Cole | |
| 9,962,100 B2 | 5/2018 | Allavatam et al. | |
| 9,993,653 B2 | 6/2018 | Bardy et al. | |
| 9,999,368 B2 | 6/2018 | Perschbacher et al. | |
| 10,004,418 B2 | 6/2018 | Cao et al. | |
| 10,183,171 B2 | 1/2019 | Ostroff et al. | |
| 10,328,274 B2 | 6/2019 | Zhang et al. | |
| 10,548,499 B2 | 2/2020 | Bayasi et al. | |
| 10,576,288 B2 | 3/2020 | Cao et al. | |
| 10,582,870 B2 | 3/2020 | Allavatam et al. | |
| 10,702,180 B2 | 7/2020 | Perschbacher et al. | |
| 10,709,379 B2 | 7/2020 | Warren et al. | |
| 2003/0204215 A1 | 10/2003 | Gunderson et al. | |
| 2007/0232948 A1 | 10/2007 | Stadler et al. | |
| 2008/0161870 A1 | 7/2008 | Gunderson | |
| 2010/0280567 A1 | 11/2010 | Gunderson | |
| 2015/0045682 A1 | 2/2015 | Sanghera et al. | |
| 2018/0264258 A1 | 9/2018 | Cheng et al. | |
| 2018/0311504 A1* | 11/2018 | Cao ..................... A61N 1/3987 |
| 2018/0318588 A1 | 11/2018 | Dennis | |
| 2019/0329038 A1 | 10/2019 | Rhude | |
| 2020/0100694 A1 | 4/2020 | Sarkar et al. | |

FOREIGN PATENT DOCUMENTS

| | | |
|---|---|---|
| EP | 1877137 B1 | 10/2014 |
| EP | 2967402 B1 | 1/2016 |
| EP | 2364107 B1 | 9/2016 |
| EP | 1219237 B1 | 2/2017 |
| EP | 3247453 B1 | 11/2017 |
| EP | 2895063 B1 | 1/2019 |
| EP | 3422934 B1 | 1/2019 |
| EP | 3432774 B1 | 1/2019 |
| EP | 3566746 A1 | 5/2019 |
| EP | 3592419 B1 | 1/2020 |
| EP | 2741662 B1 | 3/2021 |
| WO | WO03/092810 A2 | 11/2003 |
| WO | WO2019/075529 A1 | 4/2019 |

OTHER PUBLICATIONS

U.S. Appl. No. 18/146,870, filed Dec. 27, 2022.
U.S. Appl. No. 17/153,036, filed Jan. 20, 2021.
U.S. Appl. No. 17/723,207, filed Apr. 18, 2022.
U.S. Patent Application No. 17/XX filed Apr. X, 2022.
"Spontaneous T-wave oversensing," Cardiocases, Pacing & Defibrillation, [https://www.cardiocases.com/en/pacingdefibrillation/clinical-situation/icd/spontaneous-t-wave-oversensing], downloaded Jun. 1, 2021, 9 pages.
Hadjileontiadis, Leontios J., et al., "Performance of Three QRS Detection Algorithms During Sleep: A Comparative Study," 2001 Proceedings of the 23rd Annual EMBS International Conference, Oct. 25-28, 2001, 4 pages.
Pandit, Diptangshu, et al., "A lightweight QRS detector for single lead ECG signals using a max-min difference algorithm," Computer Methods and Programs in Biomedicine, 144, Feb. 2017 15 pages.
Extended European Search Report dated Oct. 19, 2021, European Patent Application No. 21170198.2-1132.
Response to Extended European Search Report dated Feb. 4, 2022, European Patent Application No. 21170198.2-1132.
International Search Report & The Written Opinion of the International Searching Authority dated Mar. 31, 2021, International Application No. PCT/US2021/014332.

* cited by examiner

METHODS, DEVICES AND SYSTEMS FOR IMPROVING R-WAVE DETECTION AND ARRHTYMIA DETECTION ACCURACY

PRIORITY CLAIM

The present application claims priority to U.S. Provisional Patent Application No. 63/033,184, filed Jun. 1, 2020, and U.S. Provisional Patent Application No. 63/034,866, filed Jun. 4, 2020, both of which are incorporated herein by reference.

FIELD OF TECHNOLOGY

Embodiments described herein relate techniques for improving R-wave detection sensitivity and positive predictive value, and more specifically, to techniques for identifying and/or correcting for P-wave oversensing, as well as techniques for identifying false arrhythmia detections, such as false atrial fibrillation (AF) detections.

BACKGROUND

Various types of implantable medical devices (IMDs) are used to monitor for cardiac arrythmias. Some types of IMDs, such as implantable cardiac pacemakers and implantable cardiac defibrillators (ICDs), are capable of providing appropriate therapy in response to detected cardiac arrythmias. Other types of IMDs, such as insertable cardiac monitors (ICMs), are used for diagnostic purposes. ICMs have been increasingly used to diagnose cardiac arrhythmias, particularly atrial fibrillation (AF).

Atrial Fibrillation (AF) is a very common type of supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices, such as ICMs, now monitor for AF by obtaining an electrogram (EGM) signal and measuring R-R interval variability based on the EGM signal. For example, an ICM or other IMD can compare measures of R-R interval variability to a variability threshold, to automatically detect AF when the variability threshold is exceeded. Indeed, ICMs predominantly identify AF by quantifying the variability in R-R intervals (i.e., by quantifying the variability in the timing of ventricular contractions).

There are a few ICMs that are commercially available, including the Confirm RX™ ICM, manufactured by Abbott Laboratories, of Chicago, Illinois, the Reveal LINQ™ ICM, manufactured by Medtronic, Inc., of Minneapolis, Minnesota, and the BioMonitor™ 3, manufactured by Biotronik SE & Co. KG, of Berlin, Germany. When an ICM detects an episode of AF, information about the episode may be recorded and a corresponding EGM segment (and/or other information) can be transmitted from the ICM to a patient care network for clinician review. False positive AF detections are highly undesirable, as the burden of sorting through large numbers of clinically irrelevant episodes of AF can be time consuming and costly.

Accurate identification of R-waves is important because many IMDs predominantly identify arrhythmias using R-R intervals, wherein an R-R interval is the time elapsed between a pair of successive R-waves in an EGM or electrocardiogram (ECG). Both oversensing and undersensing of R-waves can happen in IMDs. R-wave undersensing may cause false arrythmia detections, such as false bradycardia detections or false AF detections. R-wave oversensing may also cause false arrythmia detections, such as false tachycardia detections and/or false AF detections. R-wave oversensing may occur where a P-wave or a T-wave is mistakenly identified as an R-wave. R-wave sensing is often based on least in part on comparisons of EGM or ECG amplitudes to an R-wave detection threshold. However, because R-wave amplitudes may vary due to changes in sensing vector orientation relative to the cardiac axis, even optimized R-wave sensing programming (e.g., including an optimal setting of an R-wave detection threshold) may not be able to fully eliminate R-wave oversensing in some IMDs.

SUMMARY

Certain embodiments of the present technology are directed to methods, devices, and systems for improving R-wave detection sensitivity and positive predictive value, as well as for improving the accuracy of arrhythmia detections. A method according to an embodiment of the present technology includes detecting potential R-waves within a signal indicative of cardiac electrical activity, such as an EGM or ECG. The method also includes determining whether to classify a potential R-wave as a false R-wave by (i) determining a measure of magnitude of a first portion of the signal corresponding to a first window that follows the potential R-wave, (ii) determining the measure of magnitude of a second portion of the signal corresponding to a second window that follows the first window, (iii) determining whether the measure of magnitude of the second portion of the signal is at least a specified extent larger than the measure of magnitude of the first portion of the signal, and (iv) classifying the potential R-wave as a false R-wave, in response to determining that the measure of magnitude of the second portion of the signal is at least the specified extent larger than the measure of magnitude of the first portion of the signal. In accordance with certain embodiments, the (iv) classifying the potential R-wave as a false R-wave, comprises classifying the potential R-wave as an over-sensed P-wave. In accordance with certain embodiments, the measure of magnitude is selected from the group consisting of an absolute value of a maximum peak, a maximum peak-to-peak amplitude, an absolute value of a first derivative, or an area under a curve.

In accordance with certain embodiments, the first window starts at a first time that coincides with a marker for the potential R-wave, ends at a second time after the first time, and has a first duration. The second window starts at the second time, ends at a third time after the second time, and has a second duration that is at least twice the first duration. In certain embodiments, the first duration is within a range of 20 msec to 100 msec inclusive, and the second duration is within a range of 150 msec to 350 msec inclusive.

In accordance with certain embodiments, the specified extent larger comprises N times larger, where N has a value of at least 2, the (iii) determining comprises determining whether the measure of magnitude of the second portion of the signal is at least N times larger than the measure of magnitude of the first portion of the signal, and the (iv) classifying comprises classifying the potential R-wave as a false R-wave, in response to determining that the measure of magnitude of the second portion of the signal is at least N times larger than the measure of magnitude of the first portion of the signal. In accordance with other embodiments, the specified extent larger comprises a magnitude of M larger, the (iii) determining comprises determining whether the measure of magnitude of the second portion of the signal is at least the magnitude of M larger than the measure of magnitude of the first portion of the signal, and the (iv) classifying comprises classifying the potential R-wave as a false R-wave, in response to determining that the measure of magnitude of the second portion of the signal is at least the magnitude of M larger than the measure of magnitude of the first portion of the signal.

In accordance with certain embodiments, the detecting potential R-waves within the signal indicative of cardiac electrical activity comprises comparing the signal indicative of cardiac electrical activity, or samples thereof, to an R-wave detection threshold, and detecting potential R-waves based on the signal indicative of cardiac electrical activity, or the samples thereof, crossing the R-wave detection threshold. Each of the potential R-waves is associated with a respective temporal R-wave marker which can be indicative of when a portion of the signal indicative of cardiac electrical activity, or samples thereof, crossed the R-wave detection threshold. Additionally, the method further comprises, in response to classifying a potential R-wave as a false R-wave, adjusting the respective temporal R-wave marker for the potential R-wave to coincide with a peak in the respective second window that follows the potential R-wave.

In accordance with certain embodiments, the determining whether to classify a potential R-wave as a false R-wave is performed by an implantable medical device (IMD), for each potential R-wave of at least a subset of potential R-waves within a segment of the signal leading up to a detection by the IMD of a potential arrhythmic episode (e.g., a potential AF episode). In certain such embodiments, the method further comprises the IMD determining whether to classify the potential arrhythmic episode that was detected by the IMD as a false positive detection, based on how many of the potential R-waves within the segment are classified as a false R-wave, or more specifically, an over-sensed P-wave. Additionally, in accordance with certain such embodiments, the IMD determining whether to classify the potential arrhythmic episode that was detected by the IMD as a false positive detection, comprises: the IMD determining whether a number of potential R-waves that are classified as false R-waves (or more specifically, over-sensed P-waves), within the segment of the signal leading up to the detection by the IMD of the potential arrhythmic episode, exceeds a further threshold; and the IMD classifying the potential arrhythmic episode that was detected by the IMD as a false positive detection, based on the IMD determining that the number of potential R-waves that are classified as false R-waves (or more specifically, over-sensed P-waves) exceeds the further threshold. In accordance with certain embodiments, the method further comprises at least one of the following: the IMD preventing transmitting, to an external device that is communicatively coupled to a patient care network, data corresponding to a potential arrhythmic episode that is detected by the IMD but is thereafter determined by the IMD as being a false positive detection; the IMD allowing overwriting of stored data corresponding to the potential arrhythmic episode that was detected by the IMD but is thereafter determined by the IMD as being a false positive detection; or the IMD not storing in memory data corresponding to the potential arrhythmic episode that is detected by the IMD but is thereafter determined by the IMD as being a false positive detection.

In accordance with certain embodiments, the detecting potential R-waves within the signal indicative of cardiac electrical activity comprises comparing the signal indicative of cardiac electrical activity, or samples thereof, to an R-wave detection threshold, and detecting potential R-waves based on the signal indicative of cardiac electrical activity, or the samples thereof, crossing the R-wave detection threshold. Additionally, the determining whether to classify a potential R-wave as a false R-wave is performed by an IMD, for each potential R-wave of at least a subset of potential R-waves within a segment of the signal (e.g., a segment of a signal leading up to a detection of a potential arrhythmic episode). In certain such embodiments, the method further comprises increasing the R-wave detection threshold in response to a number of potential R-waves that are classified as being false R-waves (or more specifically, over-sensed P-waves), within the segment of the signal, exceeding a false R-wave detection threshold.

A device according to certain embodiments of the present technology comprises one or more electrodes, sensing circuitry, and at least one of a processor or controller. The sensing circuitry is coupled to the one or more electrodes and configured to obtain a signal indicative of electrical activity of a patient's heart, such as an EGM or ECG. The at least one of a processor or controller is/are configured to: detect a potential R-wave within the signal indicative of cardiac electrical activity; determine a measure of magnitude of a first portion of the signal corresponding to a first window that follows the potential R-wave; determine the measure of magnitude of a second portion of the signal corresponding to a second window that follows the first window; determine whether the measure of magnitude of the second portion of the signal is at least a specified extent larger than the measure of magnitude of the first portion of the signal; and classify the potential R-wave as a false R-wave, in response to determining that the measure of magnitude of the second portion of the signal is at least the specified extent larger than the measure of magnitude of the first portion of the signal.

In accordance with certain embodiments, each of the potential R-waves is associated with a respective temporal R-wave marker, and the at least one of a processor or controller is/are configured to adjust a respective temporal R-wave marker for the potential R-wave to coincide with a peak in the respective second window that follows the potential R-wave, in response to the potential R-wave being classified as a false R-wave, or more specifically and over-sensed P-wave.

In accordance with certain embodiments, the device comprises an IMD, and the at least one of a processor or controller is/are further configured to determine whether to classify a potential arrhythmic episode that is detected by the IMD as a false positive detection, based on how many of the potential R-waves within a window leading up the potential arrhythmic episode detection are classified as a false R-wave, or more specifically, an over-sensed P-wave. In accordance with certain embodiments, the IMD includes a telemetry circuit configured to enable the IMD to communicate with an external device, and memory configured to store data corresponding to one or more arrhythmic episodes detected by the IMD. In certain such embodiments, the at least one of a processor or controller is/are further configured to at least one of: prevent transmission by the telemetry circuit, to an external device that is communicatively coupled to a patient care network, of data corresponding to a potential arrhythmic episode that is detected by the IMD but is thereafter determined by the IMD as being a false positive detection; allow overwriting in the memory of data corresponding to a potential arrhythmic episode that was detected by the IMD but is thereafter determined by the IMD as being a false positive detection; or prevent storing in the memory of data corresponding to a potential arrhythmic episode that is detected by the IMD but is thereafter determined by the IMD as being a false positive detection.

In accordance with certain embodiments, the at least one of a processor or controller of the IMD is/are further configured to increase an R-wave detection threshold in response to a number of potential R-waves that are classified as being false R-waves, within a segment of the signal or within a specified amount of time, exceeding a false R-wave detection threshold.

A method according to an embodiment of the present technology comprises: detecting potential R-waves within a signal indicative of cardiac electrical activity, wherein each of the potential R-waves is associated with a respective temporal R-wave marker; monitoring for a potential episode of an arrhythmia based on the potential R-waves; in response to detecting the potential episode of the arrhythmia, for each of a plurality of the potential R-waves within a segment of the signal leading up to the potential episode of the arrhythmia, selectively adjusting the respective temporal R-wave marker for the potential R-wave by (i) determining a measure of magnitude of a first portion of the signal corresponding to a first window that follows the respective R-wave marker for the potential R-wave; (ii) determining the measure of magnitude of a second portion of the signal corresponding to a second window that follows the first window; (iii) determining whether the measure of magnitude of the second portion of the signal is at least a specified extent larger than the measure of magnitude of the first portion of the signal; and (iv) in response to determining that the measure of magnitude of the second portion of the signal is at least the specified extent larger than the measure of magnitude of the first portion of the signal, adjusting the respective temporal R-wave marker for the potential R-wave to coincide with a peak in the respective second window that follows the potential R-wave. Such a method can further include, in response to adjusting the respective temporal R-wave markers for at least a threshold number of potential R-waves within the segment of the signal, using the adjusted temporal R-wave markers to determine whether the detection of the potential episode of the arrhythmia was a false positive detection. In accordance with certain embodiments, the method is performed by an IMD, and the method further comprises at least one of the following: the IMD preventing transmitting, to an external device that is communicatively coupled to a patient care network, data corresponding to the potential episode of the arrhythmia that is detected by the IMD but is thereafter determined by the IMD as being a false positive detection; the IMD allowing overwriting of stored data corresponding to the potential episode of the arrhythmia that was detected by the IMD but is thereafter determined by the IMD as being a false positive detection; or the IMD not storing in memory data corresponding to the potential episode of the arrhythmia that is detected by the IMD but is thereafter determined by the IMD as being a false positive detection.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1:
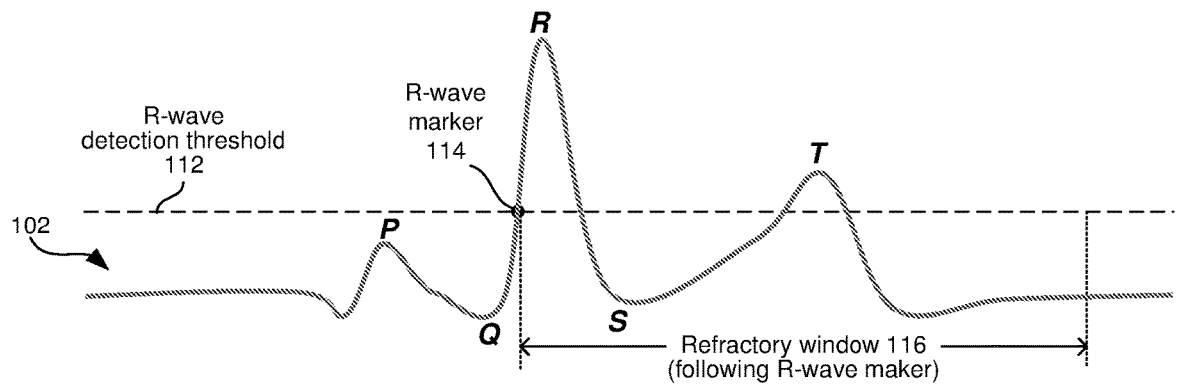
FIG. 1 includes a portion of an EGM and is used to show how a true R-wave can be detected based at least in part on the EGM crossing an R-wave detection threshold.

It is well known that each cardiac cycle represented within an EGM or ECG typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of electrical activity of a patient's heart.

The R-wave is typically the largest wave in the QRS complex, and it often identified by comparing samples of an EGM or ECG to an R-wave threshold. Various measurements can be obtained based on the EGM or ECG waveform, including measurements of R-R intervals, where an R-R interval is the duration or elapsed time between a pair of successive R-waves. As noted above, in the Background, a common technique for detecting AF is based on measures of R-R interval variability. However, for various reasons, including an implant angle of an IMD relative to the heart, the dynamically changing R-wave amplitude may occasionally be too small to detect, thereby leading to R-wave undersensing, unless clinicians lower the programmable R-wave sensing threshold to correct this. In other cases, P-wave and/or T-wave amplitudes exceeding the R-wave sensing threshold may result in R-waves undersensing. Where T-waves and/or P-waves are falsely identified as R-waves, false R-R intervals can be identified which have a high variability, leading to false detections of AF. In addition, the ICM systems also have additional algorithms designed to reject false detections of AF if presence of P-waves is identified in the EGM or ECG signal. With T-waves and/or P-waves oversensing, these additional algorithms cannot find the true P-wave segments in the EGM/ECG signal thus may fail to reject false detections of AF. In other words, over-sensed P-waves and/or over-sensed T-waves can lead to false positive AF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. An under-sensed R-wave, as the term is used herein, refers to an R-wave that is not detected. An over-sensed R-wave, as the term is used herein, refers to a feature (e.g., a P-wave or a T-wave) of an EGM or ECG that is falsely identified as an R-wave.

Figure 2:
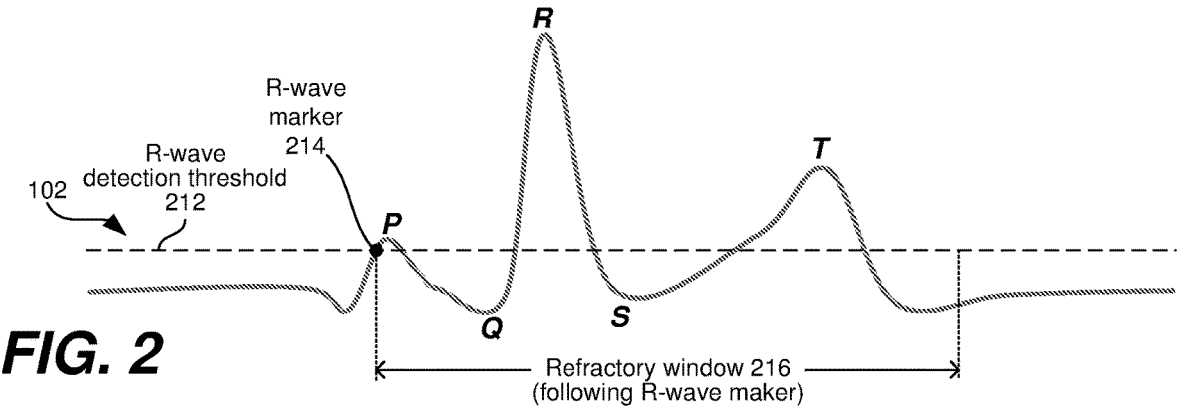
FIG. 2 includes the same portion of the EGM included in FIG. 1, and is used to show how a P-wave can be mistakenly detected as an R-wave, due to low R-wave detection threshold, which can lead to the true R-wave not being detected.
Figure 3:
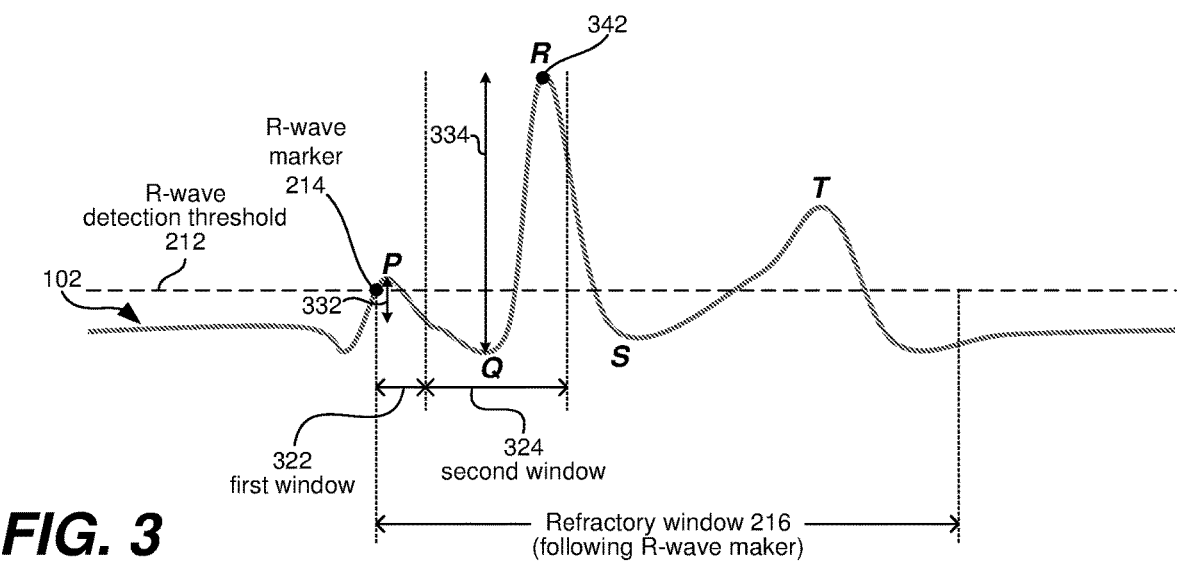
FIG. 3 includes the same portion of the EGM included in FIGS. 1 and 2, and is used to show how a P-wave that is mistakenly detected as an R-wave, can be identified as a false R-wave using an embodiment of the present technology, which can also allow for identification of the true R-wave which was initially not identified.

FIGS. 1-3 illustrate the same portion of the same EGM 102, and includes labels indicating where a P-wave, a Q-wave, an R-wave, an S-wave, and a T-wave are actually located within the portion of the EGM 102. FIG. 1 is used to show how a true R-wave can be detected based on the EGM crossing an R-wave detection threshold 112. FIG. 2 is used to show how a P-wave can be mistakenly detected as an R-wave, due to P-wave oversensing, which can lead to the true R-wave not being detected. Thereafter, FIG. 3 is used to show how a P-wave that is mistakenly detected as an R-wave, due to P-wave oversensing, can be identified as a false R-wave using an embodiment of the present technology, which can also allow for identification of the true R-wave which was initially not identified.

Referring to FIG. 1, the portion of the EGM 102 shown therein, as noted above, includes labels indicating where the P-wave, the Q-wave, the R-wave, the S-wave, and the T-wave are actually located. Also shown in FIG. 1 is a dashed line labeled 112 which is representative of an example R-wave detection threshold. Such an R-wave detection threshold 112 can be used to detect the R-wave, e.g., by identifying when the EGM 102 crosses the R-wave detection threshold, but is not limited thereto. In other words, the R-wave shown in FIG. 1 can be detected based on when the EGM 102 crosses the R-wave detection threshold 112. (It is noted that the term "based on" as used herein, unless stated otherwise, should be interpreted as meaning based at least in part on, meaning there can be one or more additional factors upon which a decision or the like is made.)

Still referring to FIG. 1, the dot labeled 114 is representative of an R-wave marker, which in this example, coincides with a crossing of the R-wave detection threshold 112 by the EGM 102. However, it may not always be the case that the R-wave marker 114 coincides with the initial crossing of the R-wave detection threshold 112 by the EGM 102. Nevertheless, what will typically be the case is that the R-wave marker 114, when correctly marking an R-wave, will mark a point in time between an immediately preceding Q-wave and a peak of an R-wave, as is the case in FIG. 1. Also shown in FIG. 1 is an exemplary refractory window 116, following the R-wave marker 114, wherein the refractory widow 116 corresponds to a period of time during which an IMD does not search or sense for an R-wave because an R-wave had just been detected. An example duration of the refractory window 116, which begins at the R-wave marker 114, is within the range of 250 msec to 300 msec, inclusive.

Referring now to FIG. 2, the portion of the EGM shown therein is the same as the portion shown FIG. 1, and thus the portion of the EGM is again labeled 102. Also shown in FIG. 2 is another example R-wave detection threshold 212, which has a lower magnitude than the R-wave detection threshold 114 shown in FIG. 1. Additionally shown in FIG. 2 is an R-wave marker 214 that incorrectly marks a portion of the P-wave as the R-wave, at least in part due to the peak of the P-wave being greater than the R-wave detection threshold 212. Following the R-wave marker 214 is the refractory window 216 during which the IMD does not search or sense for an R-wave because an R-wave had just been detected, albeit incorrectly. Note that in FIG. 2 the actual R-wave is within the refractory window 216.

Referring now to FIG. 3, the R-wave detection threshold 212, the R-wave marker 214, and the refractory window 216 are the same as they were in FIG. 2, and thus they are labeled the same as they were in FIG. 2. Also shown in FIG. 3 are first and second windows 322, 324, which are utilized in accordance with an embodiment of the present invention to determine that the detected R-wave (aka the detected potential R-wave) was actually a false R-wave detection (aka a false positive detection). The first window 322 starts at a first time that coincides with the R-wave marker 214 (or more generally, at a marker for a potential R-wave), ends at a second time after the first time, and has a first duration. An example duration of the first window is 50 msec, but other durations for the first window within the range of 20 msec to 100 msec inclusive are also possible and within the scope of the embodiments described herein. The second window 324 starts at the end of the first window 322 (i.e., at a second time), ends at a third time after the second time, and has a second duration that is at least twice the first duration. An example duration of the second window is 200 msec, but other durations for the second window within the range of 150 msec to 350 msec inclusive are also possible and within the scope of the embodiments described herein. The duration of the second window (aka the second duration) is at least twice the duration of the first window (aka the first duration), and in certain embodiments is at least three times the duration of the first window.

The portion of EGM 102 within the first window 322 can be referred to herein as a first portion of the EGM, and the portion of the EGM 102 within the second window 324 can be referred to herein as a second portion of the EGM. In accordance with certain embodiments, a maximum peak-to-peak amplitude of the first portion of the EGM (i.e., the portion of the EGM within the first window 322) and a maximum peak-to-peak amplitude of the second portion of the EGM (i.e., the portion of the EGM within the second window 324) are determined and compared to one another to determine whether the maximum peak-to-peak amplitude of the second portion of the EGM is at least a specified extent larger than the maximum peak-to-peak amplitude of the first portion of the EGM, which should only occur where an actual R-wave is within the second window 324, and thus, is indicative of the potential R-wave detection (corresponding to the R-wave marker 214) being a false R-wave, and more specifically, an over-sensed P-wave. The specified extent larger can be N times larger, where N has a value of at least 2, and examples values for N are 2, 2.25, 2.5, 2.75, and 3, but are not limited thereto. For example, where N is specified to be equal to 3, then a potential R-wave detection would be classified as a false R-wave detection where the maximum peak-to-peak amplitude of the second portion of the EGM is at least a 3 times larger than the maximum peak-to-peak amplitude of the first portion of the EGM. In FIG. 3, the vertical double arrowed line labeled 332 shows the maximum peak-to-peak amplitude of the first portion of the EGM 102, and the vertical double arrowed line labeled 334 shows the maximum peak-to-peak amplitude of the second portion of the EGM 102. In FIG. 3, the maximum peak-to-peak amplitude 332 of the second portion of the EGM is more than 3 times larger than the maximum peak-to-peak amplitude 334 of the first portion of the EGM, resulting in the potential R-wave detection (associated with the R-wave marker 314) being classified as a false R-wave, and in certain embodiments, results in the potential R-wave detection (associated with the R-wave marker 314) being classified as an over-sensed P-wave.

Instead of comparing the maximum peak-to-peak amplitude of the second portion of the EGM (i.e., the portion of the EGM within the second window 324) to the maximum peak-to-peak amplitude of the first portion of the EGM (i.e., the portion of the EGM within the first window 322), an alternative measure of magnitude of the second portion of the EGM can be compared to the alternative measure of magnitude of the first portion of the EGM. An alternative measure of magnitude is an absolute value of a maximum peak, in which case if the absolute value of the maximum peak within the second portion of the signal is at least the specified extent larger (e.g., at least 3 times larger) than the absolute value of the maximum peak within the first portion of the signal, then the potential R-wave detection (corresponding to an R-wave marker) will be classified as a false R-wave.

In an alternative embodiment, the measure of magnitude is an absolute value of a first derivative. Where the measure of magnitude is the absolute peak value of the first derivative, the first derivative of the first portion of the EGM (i.e., the portion of the EGM within the first window 322) is determined, and the first derivative of the second portion of the EGM (i.e., the portion of the EGM within the first window 322) is determined. If the absolute peak value of the first derivative of the second portion of the signal is at least the specified extent larger (e.g., at least 3 times larger) than the absolute peak value of the first derivative of the first portion of the signal, then the potential R-wave detection (corresponding to an R-wave marker) is classified as a false R-wave.

In still another alternative embodiment, the measure of magnitude is an area under the curve. Where the measure of magnitude is the area under the curve, the area under the curve of the first portion of the EGM (i.e., the portion of the EGM within the first window 322) is determined, and the area under the curve of the second portion of the EGM (i.e., the portion of the EGM within the first window 322) is determined. If the area under the curve of the second portion of the signal is at least the specified extent larger (e.g., at least 3 times larger) than the area under the curve of the first portion of the signal, then the potential R-wave detection (corresponding to an R-wave marker) is classified as a false R-wave. The use of still other measures of magnitude are possible and within the scope of the embodiments described herein.

Figure 4:
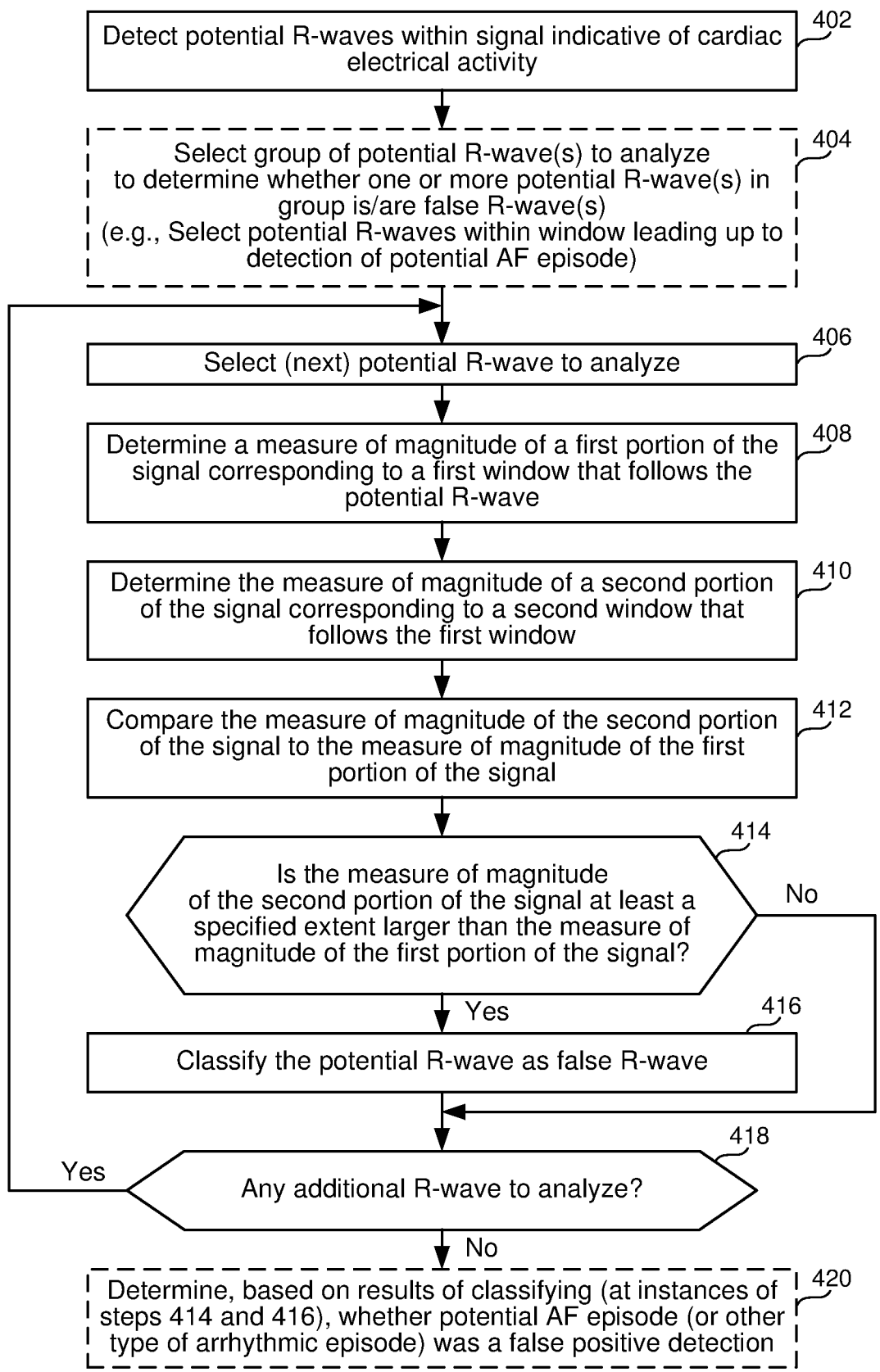
FIG. 4 includes a high level flow diagram that is used to describe how a detected potential R-wave can be classified as a false R-wave in accordance with certain embodiments of the present technology, thereby improving R-wave detection sensitivity and positive predictive value.

The high level flow diagram of FIG. 4 will now be used to summarize methods according to various embodiments of the present technology that can be used to determine whether a detected potential R-wave should be classified as a false R-wave (or more specifically an over-sensed P-wave), which embodiments can be used to improve R-wave detection sensitivity and positive predictive value. Referring to FIG. 4, step 402 involves detecting potential R-waves within a signal indicative of cardiac electrical activity, such as an EGM or ECG. Step 402 can be performed, e.g., by comparing the signal indicative of cardiac electrical activity, or samples thereof, to an R-wave detection threshold (e.g., 112 or 212), and detecting potential R-waves based on the signal indicative of cardiac electrical activity, or the samples thereof, crossing the R-wave detection threshold. Additionally, or alternatively, potential R-waves can be detecting by comparing the morphology of the signal indicative of cardiac electrical activity to an R-wave morphological template and detecting potential R-waves when there is a sufficient level of similarity or correlation between a portion of the signal and the template. Additional and/or alternative techniques for detecting potential R-waves are also possible and within the scope of the embodiments described herein. In accordance with certain embodiments, each of the potential R-waves is associated with a respective temporal R-wave marker (e.g., 114 or 214) indicative of when a portion of the signal indicative of cardiac electrical activity, or samples thereof, crossed the R-wave detection threshold, or more generally, indicative of a temporal location of the potential R-wave.

Still referring to FIG. 4, optional step 404 involves selecting a group of potential R-wave(s) to analyze to determine whether one or more potential R-wave(s) within the group is/are false R-wave(s). This step can involve, e.g., selecting potential R-waves within a window (e.g., a 30 second window) leading up to the detection of a potential AF episode, or leading up to some other detected potential arrhythmic episode.

Step 406 involves selecting a potential R-wave to analyze. Where step 404 is performed, step 406 can involve selecting one of the potential R-waves from the group that was selected at step 404. Where multiple potential R-waves are to be analyzed, the R-waves selected at instances of step 406 can be selected in a temporal order, or in a random order, but is not limited thereto.

Step 408 involves determining a measure of magnitude of a first portion of the signal corresponding to a first window (e.g., 322) that follows the potential R-wave. Step 410 involves determining the measure of magnitude of a second portion of the signal corresponding to a second window (e.g., 324) that follows the first window. Step 412 involves comparing the measure of magnitude of the second portion of the signal (corresponding to the second window and determined at step 410) to the measure of magnitude of the first portion of the signal (corresponding to the first window and determined at step 400). Step 414 involves determining whether the measure of magnitude of the second portion of the signal (determined at step 410) is at least a specified extent larger than the measure of magnitude of the first portion of the signal (determined at step 408). The order of steps 408 and 410 can be reversed, or steps 408 and 410 can be performed at the same time. Further, while steps 412 and 414 are shown as two separate steps, they can be combined into a single step.

Still referring to FIG. 4, if the answer to the determination at step 414 is Yes, then flow goes to step 416 and the potential R-wave is classified as a false R-wave. In certain embodiments the classifying the potential R-wave as a false R-wave at step 416 more specifically involves classifying the potential R-wave as an over-sensed P-wave. If the answer to the determination at step 414 is No, then flow goes to step 418, at which point there is a determination of whether there is any additional R-wave to analyze. In a specific embodiment, if the answer to the determination at step 414 is No, then flow can go to an additional step (not shown) that either classifies the potential R-wave as a true R-wave, or that increases a confidence level or probability that the potential R-wave that was analyzed is a true-R-wave. As can be appreciated from the above discussion, steps 410-416 collectively provide a way of determining whether to classify a potential R-wave as a false R-wave, and in specific embodiments, collectively provide a way of determining whether to classify a potential R-wave as an over-sensed P-wave.

If the answer to determination at step 418 is Yes, meaning that there is at least one additional R-wave to analyze, then flow returns to 406 and another potential R-wave is selected for analysis, to determine whether it should be classified as a false R-wave. If the answer to the determination at step 418 is No, then flow goes to optional step 420.

Referring to FIG. 4, step 420 is an optional step that can be used where a group of potential R-waves that were analyzed were those R-waves in a window leading up to the detection of a potential arrhythmic episode (e.g., a potential AF episode). Step 420 involves determining, based on results of the classifying (at multiple instances of steps 414 and 416), whether the potential arrhythmic episode was a false positive detection. For an example, this can involves classifying a potential AF episode as a false positive if more than a specified threshold amount (e.g., a specified number or percentage) of the potential R-waves within the window (leading up to the potential arrhythmic episode) were classified as being false R-waves. In still another embodiment, the respective the R-wave marker for each of the potential R-waves that were classified as being a false R-wave can be moved to a temporal position within the respective second window, such as to the temporal positional of the maximum peak in the second window. In other words, in response to classifying a potential R-wave as a false R-wave, the respective temporal R-wave marker for the potential R-wave can be moved to coincide with a peak in the respective second window that follows the potential R-wave. For an example, briefly referring back to FIG. 3, the temporal R-wave marker 214 can be moved to the temporal position of the dot 342, which in this example is the location of the peak in the second window 324. This would result in an updated or corrected group of potential R-waves, wherein each of the potential R-waves in the updated or corrected group is associated with a respective R-wave marker. Using this updated or corrected group, whatever arrhythmia detection algorithm was used to detect the potential arrhythmic episode (e.g., the potential AF episode) can be rerun to redetermine whether or not a potential arrhythmic episode occurred. If, after rerunning the arrhythmia detection algorithm, the potential arrhythmic episode is again detected, then the detection of the arrhythmic episode can be classified as a true detection (aka a true positive), or there can be an increase to a confidence level or probability that the potential arrhythmic episode was an actual (i.e., true) arrhythmic episode. Alternatively, the rerunning of the arrythmia detection algorithm may fail to detect an arrythmia, in which case it can be concluded that the originally detected potential arrhythmic episode was a false positive detection.

P-waves are generated by organized activation of both atrial chambers during normal sinus rhythm. Accordingly, P-waves are not present during an actual AF episode, which is associated with disorganized and chaotic atrial electric activities. In accordance with certain embodiments of the present technology, an IMD can be configured to classify a potential AF detection as a false positive (i.e., to reject an AF detection as being false) where at least a specified number N (e.g., where N is integer that has a value of at least 1) of P-waves are identified in a segment of an EGM leading up to the detection of the potential AF (aka, the potential AF detection). However, where an IMD detects an actual P-wave as an R-wave, due to P-wave oversensing, the IMD may fail to reject the potential AF detection as a false detection (aka a false positive). By utilizing embodiments of the present technology described herein to determine that one or more potentials R-wave are actually over-sensed P-waves within a window leading up to the detection of a potential AF episode, such embodiments can be used to classify the detection of a potential AF episode as a false positive detection. More specifically, in response to determining that at least a threshold number N of P-waves and/or over-sensed P-waves are including in a window (e.g., a 30 second window) leading up to the detection of the potential AF episode, the detection of the potential AF episode can be rejected or classified as being a false positive detection.

Referring back to steps 408-412, the measure of magnitude used in these steps can be, as noted above, an absolute value of a maximum peak, a maximum peak-to-peak amplitude, an absolute peak value of a first derivative, or an area under a curve, but is not limited thereto. Still referring back to steps 408-412, in accordance with certain embodiments, the first window starts at a first time that coincides with a marker for the potential R-wave, ends at a second time after the first time, and has a first duration; and the second window starts at the second time, ends at a third time after the second time, and has a second duration that is at least twice the first duration. In accordance with certain embodiments, the first duration (i.e., the duration of the first window) is within a range of 20 msec to 100 msec inclusive; and the second duration (i.e., the duration of the second window) is within a range of 150 msec to 350 msec inclusive.

Still referring back to steps 408-412, the specified extent larger referred to in these steps can be N times larger, where N has a value of at least 2. In such embodiments, step 414 involves determining whether the measure of magnitude of the second portion of the signal is at least N times larger than the measure of magnitude of the first portion of the signal, and step 416 involves classifying the potential R-wave as a false R-wave, in response to determining that the measure of magnitude of the second portion of the signal is at least N times larger than the measure of magnitude of the first portion of the signal. It is noted that determining whether the measure of magnitude of the second portion of the signal is at least 2 times larger than the measure of magnitude of the first portion of the signal, is the equivalent to determining whether the measure of magnitude of the second portion of the signal is at least 100 percent larger than the measure of magnitude of the first portion of the signal. For another example, determining whether the measure of magnitude of the second portion of the signal is at least 3 times larger than the measure of magnitude of the first portion of the signal, is the equivalent to determining whether the measure of magnitude of the second portion of the signal is at least 200 percent larger than the measure of magnitude of the first portion of the signal.

In alternative embodiments, the specified extent larger referred to in steps 408-412 is a magnitude of M larger. In such embodiments, step 414 involves determining whether the measure of magnitude of the second portion of the signal is at least a magnitude of M larger than the measure of magnitude of the first portion of the signal, and step 416 involves classifying the potential R-wave as a false R-wave, in response to determining that the measure of magnitude of the second portion of the signal is at least the magnitude of M larger the measure of magnitude of the first portion of the signal. The specific value for M, in such embodiments, can be selected for an expected range of measures of magnitude, and may be tailored to a specific device or system.

The methods described above with reference to FIG. 4 can be performed by an IMD, wherein the IMD can be an insertable cardiac monitor (ICM), a cardiac pacemaker to which one or more leads is/are attached, a leadless cardiac pacemaker (LCP), or an implantable cardioverter defibrillator (ICD), but is not limited thereto. An example of such an IMD is described below with reference to FIG. 5. Certain embodiments of the present technology are directed to such an IMD. As will be appreciated from the below discussion of FIG. 5, such an IMD (e.g., 501) can include a telemetry circuit (e.g., 564) that enables the IMD to transmit information to (or more generally, communicate with) an external device (e.g., 554), wherein the external device can be communicatively coupled to a patient care network. Using its telemetry circuit, the IMD may transmit data corresponding to an arrhythmic episode that is detected by the IMD. Additionally, the IMD can include memory (e.g., 560) that is used to store data corresponding to an arrhythmic episode, for further analysis by the IMD, and/or to later uploading to an external device (e.g. 554) using the telemetry circuit (e.g., 564). In accordance with certain embodiments, a programmer and/or controller (e.g., 520) of the IMD can be configured to prevent the transmitting, to the external device, of data corresponding to a potential arrhythmic episode that is detected by the IMD but is thereafter determined by the IMD as being a false positive detection. Additionally, or alternatively, a programmer and/or controller of the IMD can be configured to allow overwriting of stored data (e.g., stored in the memory 560) corresponding to a potential arrhythmic episode that was detected by the IMD but is thereafter determined by the IMD as being a false positive detection. In certain embodiments, a programmer and/or controller (e.g., 520) of the IMD can be configured to not store in the memory (e.g., 560) data corresponding to a potential arrhythmic episode that is detected by the IMD but is thereafter determined by the IMD as being a false positive detection.

In accordance with certain embodiments, an IMD (e.g., 501) is configured to detect potential R-waves within an EGM or ECG by comparing the EGM or ECG, or samples thereof, to an R-wave detection threshold, and can detect potential R-waves based on the EGM or ECG, or the samples thereof, crossing the R-wave detection threshold. In accordance with certain embodiments, the IMD can increase its R-wave detection threshold in response to a number of potential R-waves that are classified as being false R-waves, within a segment of an EGM or ECG, exceeding a false R-wave detection threshold.

An implementation of an embodiment of the present technology described above was tested to determine to what extend the present technology can be used to identify over-sensed P-waves that were initially identified by an IMD as R-waves. Such tests showed that embodiments of the present technology can be used to identify over 90% of over-sensed P-waves. Accordingly, embodiments of the present technology can be used to significantly improve R-wave detection sensitivity and positive predictive value, as well as to improve the accuracy of arrythmia detections that are based on R-wave detections.

The specific type of measure of magnitude, the specified extent larger, and the durations of the first and second windows, which are collectively used to determine whether to classify a potential R-wave as a false R-wave, or more specifically, an over-sensed P-wave, can be systematically optimized for a narrow patient population, a broader patient population, or for individual patients. Further, the one or more thresholds that may be used to determine whether to classify a potential arrhythmic episode (e.g., a potential AF episode) as a false positive can also be optimized for a narrow patient population, a broader patient population, or for individual patients. Accordingly, embodiments of the present technology described herein should not be limited to use with the exemplary thresholds and/or other values described herein.

Embodiments of the present technology described herein can be used with various types of IMDs, including, but not limited to, an insertable cardiac monitor (ICM), a cardiac pacemaker to which one or more leads is/are attached, a leadless cardiac pacemaker (LCP), or an implantable cardioverter defibrillator (ICD), as noted above. Such an ICD can be a transvascular ICD, or a nonvascular ICD, wherein the nonvascular ICD can be a subcutaneous (SubQ) ICD. Where embodiments of the present technology are implemented by an ICM, such embodiments can be used, e.g., to reduce the number of false positive AF detections that are transmitted from the ICM to a patient care network for clinician review. This is beneficially because false positive AF detections are highly undesirable, as the burden of sorting through large numbers of clinically irrelevant episodes of AF can be time consuming and costly. Where embodiments of the present technology are used by an ICD, or by an IMD in communication with an ICD, such embodiments can reduce how often defibrillation shocks are delivered in response to false positive AF detections. This is beneficial because defibrillation shocks are typically painful, and delivering such shocks in response to false positive AF detections subjects the patient to unnecessary shocks and may prematurely deplete the energy stored in a battery.

Embodiments of the present technology can be used together with other types of technology that can be used to identify false R-waves, and/or other types of false detections, such as over-sensed T-waves, false positive arrhythmia detections, or more generally, can be used with other techniques used for improving R-wave detection and/or arrhythmia detection and/or discrimination.

Figure 5:
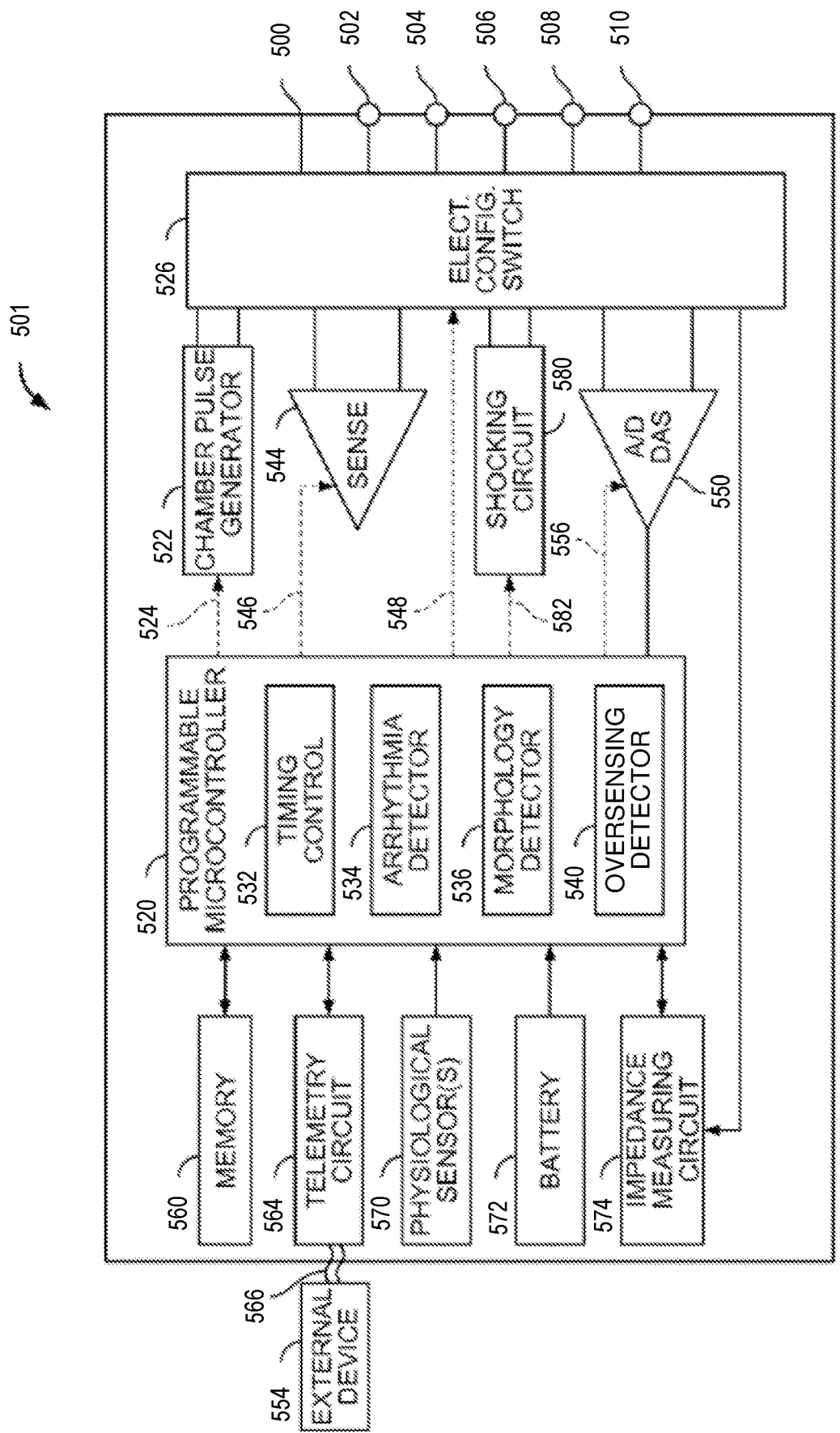
FIG. 5 shows a block diagram of one embodiment of an IMD that is implanted into a patient in accordance with certain embodiments of the present technology.

FIG. 5 shows a block diagram of one embodiment of an IMD that is implanted into a patient in accordance with a certain embodiment of the present technology. The IMD 501 may be implemented as a full-function biventricular pacemaker and defibrillator, equipped with both atrial and ventricular sensing and pacing circuitry for four chamber sensing and stimulation therapy (including both pacing and shock treatment). Optionally, the IMD 501 may provide full-function cardiac resynchronization therapy. Alternatively, the IMD 501 may be implemented with a reduced set of functions and components. For instance, the IMD may be implemented without pacing, e.g., if the IMD is an ICM. The IMD 501 can be coupled to one or more leads for single chamber or multi-chamber pacing and/or sensing. Alternatively, the IMD 501 can be an LCP that includes electrodes located on or very close to a housing 500 of the IMD 501.

The IMD 501 has a housing 500 to hold the electronic/computing components. The housing 500 (which is often referred to as the "can", "case", "encasing", or "case electrode") may be programmably selected to act as the return electrode for certain stimulus modes. The housing 500 may further include a connector (not shown) with a plurality of terminals 502, 504, 506, 508, and 510. The terminals may be connected to electrodes that are located in various locations on the housing 500 or to electrodes located on leads. The IMD 501 includes a programmable microcontroller 520 that controls various operations of the IMD 501, including cardiac monitoring and/or stimulation therapy. The microcontroller 520 includes a microprocessor (or equivalent control circuitry), RAM and/or ROM memory, logic and timing circuitry, state machine circuitry, and I/O circuitry.

The IMD 501 further includes a pulse generator 522 that generates stimulation pulses and communication pulses for delivery by one or more electrodes coupled thereto. The pulse generator 522 is controlled by the microcontroller 520 via a control signal 524. The pulse generator 522 may be coupled to the select electrode(s) via an electrode configuration switch 526, which includes multiple switches for connecting the desired electrodes to the appropriate I/O circuits, thereby facilitating electrode programmability. The switch 526 is controlled by a control signal 528 from microcontroller 520.

In the embodiment of FIG. 5, a single pulse generator 522 is illustrated. Optionally, the IMD may include multiple pulse generators, similar to the pulse generator 522, where each pulse generator is coupled to one or more electrodes and controlled by the microcontroller 520 to deliver select stimulus pulse(s) to the corresponding one or more electrodes.

The microcontroller 520 is illustrated as including timing control circuitry 532 to control the timing of the stimulation pulses (e.g., pacing rate, atrio-ventricular (AV) delay, atrial interconduction (A-A) delay, or ventricular interconduction (V-V) delay, etc.). The timing control circuitry 532 may also be used for the timing of refractory periods, blanking intervals, noise detection windows, evoked response windows, alert intervals, marker channel timing, and so on. The microcontroller 520 also has an arrhythmia detector 534 for detecting arrhythmia conditions and a morphology detector 536. Although not shown, the microcontroller 520 may further include other dedicated circuitry and/or firmware/software components that assist in monitoring various conditions of the patient's heart and managing pacing therapies. The microcontroller 520 is also shown as including an oversensing detector 540, which can be used to perform the embodiments of the present technology described above with reference to FIGS. 1-4. The oversensing detector 540 can more generally be implemented using hardware, software, firmware, and/or combinations thereof. The microcontroller can include a processor. The microcontroller, and/or the processor thereof, can be used to perform the methods of the present technology described herein.

The IMD 501 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 520, or as software/firmware instructions programmed into and executed by the microcontroller 520. Alternatively, the modem may reside separately from the microcontroller as a standalone component.

The IMD 501 includes a sensing circuit 544 selectively coupled to one or more electrodes, that perform sensing operations, through the switch 526 to detect the presence of cardiac activity in the right chambers of the heart. The sensing circuit 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 526 determines the sensing polarity of the cardiac signal by selectively closing the appropriate switches. In this way, the clinician may program the sensing polarity independent of the stimulation polarity.

The output of the sensing circuit 544 is connected to the microcontroller 520 which, in turn, triggers or inhibits the pulse generator 522 in response to the presence or absence of cardiac activity. The sensing circuit 544 receives a control signal 546 from the microcontroller 520 for purposes of controlling the gain, threshold, polarization charge removal circuitry (not shown), and the timing of any blocking circuitry (not shown) coupled to the inputs of the sensing circuitry.

In the embodiment of FIG. 5, a single sensing circuit 544 is illustrated. Optionally, the IMD may include multiple sensing circuits, similar to the sensing circuit 544, where each sensing circuit is coupled to one or more electrodes and controlled by the microcontroller 520 to sense electrical activity detected at the corresponding one or more electrodes. The sensing circuit 544 may operate in a unipolar sensing configuration or in a bipolar sensing configuration.

The IMD 501 further includes an analog-to-digital (A/D) data acquisition system (DAS) 550 coupled to one or more electrodes via the switch 526 to sample cardiac signals across any pair of desired electrodes. Data acquisition system 550 is configured to acquire intracardiac electrogram signals, convert the raw analog data into digital data, and store the digital data for later processing and/or telemetric transmission to an external device 554 (e.g., a programmer, local transceiver, or a diagnostic system analyzer). Data acquisition system 550 is controlled by a control signal 556 from the microcontroller 520.

The microcontroller 520 is coupled to a memory 560 by a suitable data/address bus. The programmable operating parameters used by the microcontroller 520 are stored in memory 560 and used to customize the operation of the IMD 501 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 501 may be non-invasively programmed into memory 560 through a telemetry circuit 564 in telemetric communication via a communication link 566 with an external device 554. The telemetry circuit 564 allows intracardiac electrograms and status information relating to the operation of the IMD 501 (as contained in the microcontroller 520 or memory 560) to be sent to the external device 554 through the communication link 566. The memory 560 can also be used to store data indicative of R-wave and/or arrhythmic episodes, and/or the like.

The IMD 501 can further include magnet detection circuitry (not shown), coupled to the microcontroller 520, to detect when a magnet is placed over the unit. A magnet may be used by a clinician to perform various test functions of IMD 501 and/or to signal the microcontroller 520 that the external device 554 is in place to receive or transmit data to the microcontroller 520 through the telemetry circuit 564.

The IMD 501 can further include one or more physiological sensors 570. Such sensors are commonly referred to as "rate-responsive" sensors because they are typically used to adjust pacing stimulation rates according to the exercise state of the patient. However, the physiological sensor(s) 570 may further be used to detect changes in cardiac output, changes in the physiological condition of the heart, or diurnal changes in activity (e.g., detecting sleep and wake states). Signals generated by the physiological sensor(s) 570 are passed to the microcontroller 520 for analysis. The microcontroller 520 responds by adjusting the various pacing parameters (such as rate, AV Delay, V-V Delay, etc.) at which the atrial and ventricular pacing pulses are administered. While shown as being included within the IMD 501, one or more physiological sensor(s) 570 may be external to the IMD 501, yet still be implanted within or carried by the patient. Examples of physiologic sensors include sensors that, for example, sense respiration rate, pH of blood, ventricular gradient, activity, position/posture, minute ventilation (MV), and so forth.

A battery 572 provides operating power to all of the components in the IMD 501. The battery 572 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 572 also desirably has a predictable discharge characteristic so that elective replacement time can be detected. As one example, the IMD 501 employs lithium/silver vanadium oxide batteries.

The IMD 501 further includes an impedance measuring circuit 574, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 574 is coupled to the switch 526 so that any desired electrode may be used. In this embodiment the IMD 501 further includes a shocking circuit 580 coupled to the microcontroller 520 by a data/address bus 582.

The embodiments of the present technology described above were primarily described as being used with an implantable medical device or system that monitors heart rate (HR) and/or for one or more types of arrhythmic episodes based on sensed potential R-waves, which as noted above can be false R-waves, and more specifically, can be over-sensed P-waves. Such embodiments of the present technology can alternatively be used with a non-implantable device or system (aka an external device or system) that includes at least two electrodes in contact with a person's skin and is used to monitor HR and/or for one or more types of arrhythmic episodes based on R-waves, and potentially R-R intervals determined therefrom. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuity coupled to the electrodes and configured to obtain a signal indicative of electrical activity of a patient's heart, and at least one of a processor or controller that is configured to perform one or more of the algorithms described above. Such a user wearable device (or more generally an external device or system) can monitor for AF and/or other types of arrythmia(s) and determine when there is a false positive detection. Additionally, or alternatively, such a user wearable device (or more generally an external device or system) can monitor a person's HR and determine when measures of HR are likely inaccurate due to oversensing. A user wearable device can both obtain a signal indicative of electrical activity of a patient's heart and monitor a person's HR and/or for arrythmia(s) based on R-R intervals determined based on R-waves within the obtained signal. Alternatively, a user wearable device can be communicatively coupled to another external device, such as a smartphone or tablet computer, and the other external device can obtain the signal from the user wearable device and monitor a person's HR and/or for arrythmia(s) based on R-waves and/or R-R intervals determined therefrom. The user wearable device or other external device or system can determine when there may be a false positive arrhythmia detection and/or when a measured HR may be inaccurate due to oversensing. Other implementations of such an external device or system are also possible and within the scope of the embodiments described herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 4. For another example, it is possible to change the boundaries of some of the blocks shown in FIG. 5.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for improving R-wave detection sensitivity and positive predictive value, comprising:
   detecting a potential R-wave within a signal indicative of cardiac electrical activity;
   determining whether to classify the potential R-wave as a false R-wave by
   (i) determining a measure of magnitude of a first portion of the signal corresponding to a first window that follows the potential R-wave;
   (ii) determining the measure of magnitude of a second portion of the signal corresponding to a second window that follows the first window;
   (iii) determining whether the measure of magnitude of the second portion of the signal is at least a specified extent larger than the measure of magnitude of the first portion of the signal; and
   (iv) classifying the potential R-wave as a false R-wave, in response to determining that the measure of magnitude of the second portion of the signal is at least the specified extent larger than the measure of magnitude of the first portion of the signal.

2. The method of claim 1, wherein the measure of magnitude is selected from the group consisting of:
   an absolute value of a maximum peak;
   a maximum peak-to-peak amplitude;
   an absolute value of a first derivative; or
   an area under a curve.

3. The method of claim 1, wherein:
   the first window starts at a first time that coincides with a marker for the potential R-wave, ends at a second time after the first time, and has a first duration; and
   the second window starts at the second time, ends at a third time after the second time, and has a second duration that is at least twice the first duration.

4. The method of claim 3, wherein:
   the first duration is within a range of 20 msec to 100 msec inclusive; and
   the second duration is within a range of 150 msec to 350 msec inclusive.

5. The method of claim 1, wherein:
   the specified extent larger comprises N times larger, where N has a value of at least 2;
   the (iii) determining comprises determining whether the measure of magnitude of the second portion of the signal is at least N times larger than the measure of magnitude of the first portion of the signal; and
   the (iv) classifying comprises classifying the potential R-wave as a false R-wave, in response to determining that the measure of magnitude of the second portion of the signal is at least N times larger than the measure of magnitude of the first portion of the signal.

6. The method of claim 1, wherein:
   the specified extent larger comprises a magnitude of M larger;
   the (iii) determining comprises determining whether the measure of magnitude of the second portion of the signal is at least the magnitude of M larger than the measure of magnitude of the first portion of the signal; and
   the (iv) classifying comprises classifying the potential R-wave as a false R-wave, in response to determining that the measure of magnitude of the second portion of the signal is at least the magnitude of M larger than the measure of magnitude of the first portion of the signal.

7. The method of claim 1, wherein:
   the (iv) classifying the potential R-wave as a false R-wave, comprises classifying the potential R-wave as an over-sensed P-wave.

8. The method of claim 1, wherein:
   the detecting the potential R-wave within the signal indicative of cardiac electrical activity comprises comparing the signal indicative of cardiac electrical activity, or samples thereof, to an R-wave detection threshold, and detecting the potential R-wave based on the signal indicative of cardiac electrical activity, or the samples thereof, crossing the R-wave detection threshold;
   the potential R-wave is associated with a respective temporal R-wave marker; and
   the method further comprises, in response to classifying the potential R-wave as a false R-wave, adjusting the respective temporal R-wave marker for the potential R-wave to coincide with a peak in the respective second window that follows the potential R-wave.

9. The method of claim 1, wherein:
   the determining whether to classify the potential R-wave as a false R-wave is performed by an implantable medical device (IMD), for each potential R-wave of at least a subset of potential R-waves within a segment of the signal leading up to a detection by the IMD of a potential arrhythmic episode; and
   the method further comprises the IMD determining whether to classify the potential arrhythmic episode that was detected by the IMD as a false positive detection, based on how many of the potential R-waves within the segment are classified as a false R-wave.

10. The method of claim 9, wherein the IMD determining whether to classify the potential arrhythmic episode that was detected by the IMD as a false positive detection, comprises:
    the IMD determining whether a number of potential R-waves that are classified as false R-waves, within the segment of the signal leading up to the detection by the IMD of the potential arrhythmic episode, exceeds a further threshold; and
    the IMD classifying the potential arrhythmic episode that was detected by the IMD as a false positive detection, based on the IMD determining that the number of potential R-waves that are classified as false R-waves exceeds the further threshold.

11. The method of claim 9, the method further comprising at least one of the following:
    the IMD preventing transmitting, to an external device that is communicatively coupled to a patient care network, data corresponding to a potential arrhythmic episode that is detected by the IMD but is thereafter determined by the IMD as being a false positive detection;
    the IMD allowing overwriting of stored data corresponding to the potential arrhythmic episode that was detected by the IMD but is thereafter determined by the IMD as being a false positive detection; or
    the IMD not storing in memory data corresponding to the potential arrhythmic episode that is detected by the IMD but is thereafter determined by the IMD as being a false positive detection.

12. The method of claim 1, wherein:
    the detecting the potential R-wave within the signal indicative of cardiac electrical activity comprises comparing the signal indicative of cardiac electrical activity, or samples thereof, to an R-wave detection threshold, and detecting the potential R-wave based on the signal indicative of cardiac electrical activity, or the samples thereof, crossing the R-wave detection threshold;

the determining whether to classify the potential R-wave as a false R-wave is performed by an implantable medical device (IMD), for each potential R-wave of at least a subset of potential R-waves within a segment of the signal; and the method further comprises increasing the R-wave detection threshold in response to a number of potential R-waves that are classified as being false R-waves, within the segment of the signal, exceeding a false R-wave detection threshold.

13. A device, comprising:
one or more electrodes;
a sensing circuitry coupled to the one or more electrodes and configured to obtain a signal indicative of cardiac electrical activity; and
at least one of a processor or controller configured to
  detect a potential R-wave within the signal indicative of cardiac electrical activity;
  determine a measure of magnitude of a first portion of the signal corresponding to a first window that follows the potential R-wave;
  determine the measure of magnitude of a second portion of the signal corresponding to a second window that follows the first window;
  determine whether the measure of magnitude of the second portion of the signal is at least a specified extent larger than the measure of magnitude of the first portion of the signal; and
  classify the potential R-wave as a false R-wave, in response to determining that the measure of magnitude of the second portion of the signal is at least the specified extent larger than the measure of magnitude of the first portion of the signal.

14. The device of claim 13, wherein the measure of magnitude is selected from the group consisting of:
an absolute value of a maximum peak;
a maximum peak-to-peak amplitude;
an absolute value of a first derivative; or
an area under a curve.

15. The device of claim 13, wherein:
the first window starts at a first time that coincides with a marker for the potential R-wave, ends at a second time after the first time, and has a first duration;
the second window starts at the second time, ends at a third time after the second time, and has a second duration that is at least twice the first duration;
the first duration is within a range of 20 msec to 100 msec inclusive; and
the second duration is within a range of 150 msec to 350 msec inclusive.

16. The device of claim 13, wherein:
the specified extent larger comprises N times larger, where N has a value of at least 2.

17. The device of claim 13, wherein the potential R-wave is associated with a respective temporal R-wave marker, and wherein the at least one of a processor or controller is/are configured to adjust the respective temporal R-wave marker for the potential R-wave to coincide with a peak in the respective second window that follows the potential R-wave, in response to the potential R-wave being classified as a false R-wave.

18. The device of claim 13, wherein the device comprises an implantable medical device (IMD), and wherein the at least one of a processor or controller is/are further configured to:
determine whether to classify a potential arrhythmic episode that is detected by the IMD as a false positive detection, based on how many potential R-waves within a window leading up the potential arrhythmic episode that is detected are classified as a false R-wave.

19. The device of claim 18, wherein the IMD includes a telemetry circuit configured to enable the IMD to communicate with an external device, and memory configured to store data corresponding to one or arrhythmic episodes detected by the IMD, and wherein the at least one of a processor or controller is/are further configured to at least one of:
prevent transmission by the telemetry circuit, to an external device that is communicatively coupled to a patient care network, of data corresponding to a potential arrhythmic episode that is detected by the IMD but is thereafter determined by the IMD as being a false positive detection;
allow overwriting in the memory of data corresponding to a potential arrhythmic episode that was detected by the IMD but is thereafter determined by the IMD as being a false positive detection; or
prevent storing in the memory of data corresponding to a potential arrhythmic episode that is detected by the IMD but is thereafter determined by the IMD as being a false positive detection.

20. The device of claim 18, wherein the at least one of a processor or controller is/are further configured to increase an R-wave detection threshold in response to a number of potential R-waves that are classified as being false R-waves, within a segment of the signal or within a specified amount of time, exceeding a false R-wave detection threshold.

21. A method, comprising:
detecting potential R-waves within a signal indicative of cardiac electrical activity, wherein each of the potential R-waves is associated with a respective temporal R-wave marker;
monitoring for a potential episode of an arrhythmia based on the potential R-waves;
in response to detecting a potential episode of the arrhythmia, for each potential R-wave of a plurality of the potential R-waves within a segment of the signal leading up to the potential episode of the arrhythmia, selectively adjusting the respective temporal R-wave marker for the potential R-wave by
  (i) determining a measure of magnitude of a first portion of the signal corresponding to a first window that follows the respective R-wave marker for the potential R-wave;
  (ii) determining the measure of magnitude of a second portion of the signal corresponding to a second window that follows the first window;
  (iii) determining whether the measure of magnitude of the second portion of the signal is at least a specified extent larger than the measure of magnitude of the first portion of the signal; and
  (iv) in response to determining that the measure of magnitude of the second portion of the signal is at least the specified extent larger than the measure of magnitude of the first portion of the signal, adjusting the respective temporal R-wave marker for the potential R-wave to coincide with a temporal position within the respective second window that follows the potential R-wave; and in response to adjusting the respective temporal R-wave markers for at least a threshold number of potential R-waves within the segment of the signal, using the adjusted temporal R-wave markers to determine whether the detection of the potential episode of the arrhythmia was a false positive detection.

22. The method of claim 21, wherein the method is performed by an implantable medical device (IMD), and the method further comprises at least one of the following:

the IMD preventing transmitting, to an external device that is communicatively coupled to a patient care network, data corresponding to the potential episode of the arrhythmia that is detected by the IMD but is thereafter determined by the IMD as being a false positive detection;

the IMD allowing overwriting of stored data corresponding to the potential episode of the arrhythmia that was detected by the IMD but is thereafter determined by the IMD as being a false positive detection; or the IMD not storing in memory data corresponding to the potential episode of the arrhythmia that is detected by the IMD but is thereafter determined by the IMD as being a false positive detection.

* * * * *